United States Patent [19]

Nishikido et al.

[11] 4,146,730

[45] Mar. 27, 1979

[54] METHOD FOR OBTAINING GLUTARIC ACID, SUCCINIC ACID, AND ADIPIC ACID FROM AN ACID MIXTURE COMPRISING THEM

[75] Inventors: Joji Nishikido; Nobuhiro Tamura; Yohei Fukuoka, all of Fuji, Japan

[73] Assignee: Asahi Kasei Kogyo Kabushiki Kaisha, Osaka, Japan

[21] Appl. No.: 750,703

[22] Filed: Dec. 15, 1976

[30] Foreign Application Priority Data

Dec. 25, 1975 [JP] Japan ................................ 50/154052
Mar. 29, 1976 [JP] Japan ................................ 51/33559
Mar. 29, 1976 [JP] Japan ................................ 51/33560

[51] Int. Cl.[2] ................................ C07C 51/42

[52] U.S. Cl. ................................ 562/513; 562/530; 562/543; 562/593

[58] Field of Search ........... 260/537 R, 537 P, 527 R; 562/513, 530, 543, 593

[56] References Cited

U.S. PATENT DOCUMENTS 2,569,984 10/1951 Fetterly ........................... 260/526 N
2,588,602 3/1952 Adams et al. ..................... 260/643 R

*Primary Examiner*—Vivian Garner

*Attorney, Agent, or Firm*—Armstrong, Nikaido, Marmelstein & Kubovcik

[57] ABSTRACT

A method for obtaining glutaric acid, succinic acid, and adipic acid from an acid mixture obtained as a by-product in the industry and comprising glutaric acid, succinic acid and adipic acid, which comprises the steps of: (1) contacting the acid mixture with urea of 1 to 2 moles per mole of the acid mixture, in solution, to deposit a urea-glutaric acid adduct so that the weight ratio of glutaric acid remaining in the solution to succinic acid is 1.2 or less when the adipic acid content is in the range of 0% by weight to 7% by weight and 1.4 or less when the adipic acid content is larger than 7% by weight and 30% by weight or less; separating the deposited urea-glutaric acid adduct out of the solution; (2) adding further urea to the solution and/or concentrating the solution obtained in the step (1) to deposit a urea-succinic acid adduct; separating the deposited urea-succinic acid adduct out of the solution; and (3) decomposing the separated urea-dicarboxylic acid adducts each into respective dicarboxylic acids and urea. With this method, the mixture comprising glutaric acid, succinic acid and adipic acid can, for the first time, be successfully and effectively separated into the respective components.

18 Claims, No Drawings

METHOD FOR OBTAINING GLUTARIC ACID, SUCCINIC ACID, AND ADIPIC ACID FROM AN ACID MIXTURE COMPRISING THEM

This invention relates to a method of treating an acid mixture obtained as a by-product in the industry and more particularly to a method of separately obtaining glutaric acid, succinic acid and adipic acid from a mixture thereof.

A by-product obtained in the production of an adipic acid is one of the typical examples of an acid mixture which comprises glutaric acid, succinic acid and adipic acid. Stated illustratively, adipic acid is industrially produced generally by oxidizing a mixture of cyclohexanone and cyclohexanol with nitric acid. During the oxidation reaction, glutaric acid and succinic acid are produced as by-products. Further, an appreciable amount of adipic acid is discharged without being recovered. Thus, a considerable amount of dicarboxylic acids is discharged in the above process. The dicarboxylic acids are discharged in the form of an acid mixture composed mainly of glutaric acid, succinic acid and adipic acid and generally having the following composition: 50 to 75% by weight of glutaric acid; 15 to 35% by weight of succinic acid; and 0 to 30% by weight of adipic acid.

These dicarboxylic acids thus discharged provide one of the most serious problems. At present, the discharged dicarboxylic acids are burnt or discharged as they are without any treatment, causing environmental polution and economical waste. Under these circumstances, if each dicarboxylic acid component can be separated and recovered from the discharged dicarboxylic acid mixture for reutilization, it would provide a large industrial advantage.

The discharged acid mixture as mentioned above is colored brown, contains residual catalysts and has an unpleasant smell. It is very difficult and troublesome to separate and recover even one dicarboxylic acid component from the acid mixture to obtain isolated dicarboxylic acid of high quality by conventional techniques as proposed heretofore. For example, the conventional extraction-separation method by organic solvent or fractional distillation method cannot successfully separate or recover any one component by one operation and requires multi-stage operations to isolate one component. Thus, the separation and recovery processes in the conventional methods are very complicated and troublesome and they cannot be practiced on an industrial scale.

One object of the present invention is to provide a method of treating a dicarboxylic acid mixture for reutilizing a dicarboxylic acid contained in the mixture.

Another object of the present invention is to provide a simplified method for separately obtaining glutaric acid, succinic acid and adipic acid out of the acid mixture containing the same.

A further object of the present invention is to provide a method for obtaining glutaric acid, succinic acid and adipic acid of high purity in high yield.

Various further and more specific features and advantages of the invention will appear from the description below.

According to the present invention, there is provided a method for obtaining glutaric acid, succinic acid, and adipic acid from an acid mixture obtained as a by-product in the industry and comprising 50 to 75% by weight based on the mixture of glutaric acid, 15 to 35% by weight based on the mixture of succinic acid and 0 to 30% by weight based on the mixture of adipic acid, which comprises the steps of:

(1) contacting the acid mixture with urea in solution to deposit a urea-glutaric acid adduct so that the weight ratio of glutaric acid remaining in the solution to succinic acid is 1.2 or less when the adipic acid content is in the range of 0% by weight to 7% by weight and 1.4 or less when the adipic acid content is larger than 7% by weight and 30% by weight or less;

the urea being employed in an amount of 1 to 2 moles per mole of the acid mixture;

separating the deposited urea-glutaric acid adduct out of the solution;

(2) adding another urea to the solution and/or concentrating the solution obtained in the step (1) to deposit a urea-succinic acid adduct;

separating the deposited urea-succinic acid adduct out of the solution; and (3) decomposing the separated urea-dicarboxylic acid adducts each into respective dicarboxylic acids and urea.

The process of the present invention comprises treating in solution an acid mixture which contains 50 to 75% by weight based on the mixture of glutaric acid, 15 to 35% by weight based on the mixture of succinic acid and 0 to 30% by weight based on the mixture of adipic acid with urea employed in an amount of 1 to 2 moles per mole of the mixture to deposit the glutaric acid component in the form of a urea-glutaric acid adduct and may further comprise treating the mother liquor, with the above-obtained urea-glutaric acid adduct removed, with urea further employed in an amount of 0.2 to 2.0 moles per mole of the starting acid mixture and/or concentrating the mother liquor to deposit the succinic acid component in the form of a urea-succinic acid adduct, leaving the adipic acid component in situ. The thus obtained urea-dicarboxylic acid adducts may each be easily decomposed into respective dicarboxylic acids and urea.

This invention has such remarkable advantages that the urea adducts formed in the process of this invention so readily crystallize as to easily deposit in a short time and be easily separated by filtration without causing any clogging trouble. Further, the coloring substances, metals (residual catalysts), smelling substances, etc. contained in the acid mixture are advantageously concentrated into the mother liquor and do not any longer contaminate the urea adducts. Thus, the present invention can realize separation of urea-dicarboxylic acid adducts with high quality from the acid mixture by a simplified process. Such adducts can be in turn decomposed to respective dicarboxylic acids and urea in a manner as mentioned in detail later.

The amount of urea to be employed in the step (1) for treating the starting acid mixture may be preferably 1 to 2 moles per mole of the acid mixture. More preferably, the amount of the urea may be 1.2 to 1.5 moles per mole of the acid mixture when the adipic acid content in the mixture is 0% by weight to 7% by weight and more than 1.5 moles and 1.8 moles or less when the adipic acid content is more than 7% by weight and 30% by weight or less. In case the amount of urea employed for treating the starting mixture is smaller than 1 mole per mole of the mixture, recovery of the glutaric acid component will decrease and a considerable amount of glutaric acid will remain in the mother liquor to adversely affect the subsequent separations of succinic acid and adipic acid components. In case the amount of urea employed for treating the starting mixture is larger than 2 moles per mole of the mixture, a urea-succinic acid adduct will be crystallized out concurrently with the urea-glutaric acid adduct, contaminating with each other, so that it becomes difficult to recover glutaric acid of high purity from the thus obtained urea adducts. The urea-glutaric acid adduct is allowed to deposit so that the weight ratio of the glutaric acid remaining in the solution to the succinic acid is 1.2 or less when the adipic acid content of the acid mixture is 0 to 7% by weight and 1.4 or less when the adipic acid content is more than 7% by weight and 30% by weight or less.

In order to separate the succinic acid component from the adipic acid component remaining in the mother liquor, urea is further added, advantageously in an amount of 0.2 to 2.0 moles per mole of the starting acid mixture, to the mother liquor with the glutaric acid adduct removed. The urea is dissolved in the mother liquor under heating and then the liquor is cooled until a urea-succinic acid adduct is deposited, while leaving the adipic acid component in the liquor. Alternatively or in combination with the urea employment, the mother liquor with the urea-glutaric acid adduct removed may be concentrated. In concentration, urea remaining in the liquor reacts with succinic acid and the urea-succinic acid adduct is deposited selectively, leaving the adipic acid component in the liquor. Though the degree of concentration necessary to deposit the urea-succinic acid adduct may be varied depending on the concentration of the starting acid mixture solution and the amount of urea added, generally the urea-succinic acid adduct is selectively deposited, leaving the adipic acid component in the liquor when concentrated by $\frac{1}{4}$ to $\frac{3}{4}$.

The selectivity in separation of a glutaric acid component and a succinic acid component depends upon the adipic acid content in the acid mixture. Generally, when the adipic acid content is more than 7% by weight and 30% by weight or less, the selectivity in separation of a glutaric acid component and a succinic acid component is increased and when the adipic acid content is 7% by weight or less, the selectivity is decreased. For this reason, the above-mentioned range of the ratio of glutaric acid to succinic acid is advantageously employed in the step (2) for effective separation of a urea-glutaric acid adduct and a urea-succinic acid adduct.

The moles of the acid mixture used in the present invention indicates a total of the moles of glutaric acid, succinic acid and adipic acid in the acid mixture. Each component of the acid mixture is determined by gas chromatography after the acid mixture has been methyl-esterified.

The acid mixture subjected to the treatment of the present invention may contain other components than glutaric acid, succinic acid and adipic acid. Generally, it may be said that the more the total of the moles of glutaric acid, succinic acid and adipic acid, the higher the recovery of the respective acids becomes. However, generally, when the total of the moles of the three components is more than 90%, the recovery is not much varied.

The acid mixture and the urea are contacted in solution. The solvents for the acid mixture to be employed in the present invention may be selected from ones in which the dicarboxylic acids and urea can be dissolved and urea-dicarboxylic acid adducts are hardly soluble and with which the urea-dicarboxylic acid adducts do not react. As typical examples of the solvents employed in the present invention, there may be mentioned water and various organic solvents such as alcohols; ketones, for example, acetone, methyl ethyl ketone; esters, for example, ethyl acetate, methyl acetate; etc. As organic solvents, alcohols such as methanol, ethanol, propanol, etc. may advantageously be employed. These organic solvents may be employed in combination with water. Water or methanol or a mixed system thereof may preferably be employed and water may most suitably be employed.

The solution of the acid mixture and urea may be prepared by combining an acid mixture solution and urea, by combining acid mixture, urea and a solvent or by combining an acid mixture solution and a urea solution. The concentration of the acid mixture in the thus formed solution may generally be 5% by weight or more. In case an aqueous solution of the acid mixture is formed, the concentration may be 5 to 40% by weight and advantageously be 25 to 35% by weight. In case an organic solvent, especially, methanol, is employed, the concentration may be 5 to 30% by weight and advantageously 10 to 25% by weight.

The urea-dicarboxylic acid adducts are decomposed by a novel method suitably adapted to the present invention, to wit, a method in which an ion exchange resin is employed or a method in which an alicyclic ether is used.

According to a method in which an ion exchange resin is employed, the urea-dicarboxylic acid adducts are dissolved in water or an organic solvent such as methanol, ethanol, etc. and treated with the ion exchange resin to easily decompose the urea-dicarboxylic acid adducts to dicarboxylic acids and urea. In order to obtain free dicarboxylic acids, the solution of the urea-dicarboxylic acid adduct is treated with a strongly acidic ion exchange resin to adsorb urea on the ion exchange resin and obtain a free dicarboxylic acid. Alternatively, the urea-dicarboxylic acid adducts may be treated with a basic ion exchange resin to adsorb dicarboxylic acids on the ion exchange resin, separating from free urea and then the ion exchange resin may be treated with a strong acid such as sulfuric acid, hydrochloric acid, etc. to obtain free dicarboxylic acids. However, the method in which the strongly acidic ion exchange resin is employed is more convenient and suitable for industrial use in that dicarboxylic acids can be obtained directly and that the ion exchange resin employed is durable and can advantageously be repeatedly reclaimed. This method further has an advantage that the urea adsorbed on the strongly acidic ion exchange resin can be readily desorbed by water or organic solvents to easily reclaim the ion exchange resin. The desorbed urea may be recycled to the urea to be employed for treatment of the starting acid mixture in the step (1) and/or the mother liquor with the urea-glutaric acid adduct removed in the step (2). In case the solvent used for the ion exchange treatment is water or the same solvent as used to form the starting acid mixture solution, the urea, which is obtained in the form of a solution, may be recycled after being concentrated. In case the solvent used for the ion exchange treatment is different from that used to form the starting acid mixture solution, the obtained urea solution may be recycled after removal of the solvent.

According to an alternative method for decomposing the urea-dicarboxylic acid adducts, an alicyclic ether is employed. As an alicyclic ether, dioxane, tetrahydrofuran, dioxolan, etc. are advantageously employed in an amount of a 5 to 10 multiple of the respective adduct. For example, when the alicyclic ether is added to urea-dicarboxylic acid adducts, heated at 30° to 120° C. for 30 minutes to 5 hours and then cooled, the urea-dicarboxylic acid adducts are decomposed to dicarboxylic acids and urea, the urea is crystallized out of the solution so that the urea may be separated in the form of a solid and the obtained urea may be recycled. The dicarboxylic acid remaining in the mother liquor is obtained by concentrating the liquor or distilling off the solvent.

The process for separation of the components of the acid mixture is exemplified as follows.

An acid mixture is dissolved in water under heating to prepare a solution of the acid mixture of 5 to 40% by weight. Urea is added to the solution in an amount of 1 to 2 moles per mole of the acid mixture and dissolved therein at 50 to 100° C. When the solution is then cooled at 5° to 40° C. for 10 to 200 minutes, a urea-glutaric acid adduct is deposited. The urea-glutaric acid adduct is recovered by filtration. Urea is further added to the mother liquor in an amount of 0.2 to 2.0 moles per mole of the starting acid mixture and dissolved at 50° to 100° C. The solution is then cooled at 5° to 40° C. for 1 to 10 hours to crystallize out a urea-succinic acid adduct, which is subsequently separated by filtration.

The optimum conditions for separation of glutaric acid, succinic acid and adipic acid are varied depending upon the composition of the acid mixture, concentration, temperature and time for crystallization, amount of urea employed, adipic acid content in the mixture, etc. Therefore, each condition may be suitably selected according to other conditions to attain the effect of the present invention and is not limited to one as given herein.

From the thus obtained urea-glutaric acid adduct, urea is removed, for example, by a strongly acidic ion exchange resin to obtain high purity glutaric acid. Similarly, from the urea-succinic acid adduct, a succinic acid is obtained.

The mother liquor with the urea-succinic acid adduct removed is also treated with the strongly acidic ion exchange resin to separate and remove urea by filtration. The resulting filtrate is concentrated and cooled until a crude adipic acid is deposited. Alternatively, the mother liquor may be concentrated and then cooled to crystallize crude adipic acid and urea-adipic acid adduct out of the liquor and the obtained mixture of crude adipic acid and urea-adipic acid adduct may be treated by an ion exchange resin or an alicyclic ether to give urea and crude adipic acid.

Since coloring substances, metals (residual catalysts), smelling substances, etc. contained in the acid mixture are present in concentrated form in the mother liquor having the adipic acid component, the obtained crude adipic acid needs to be recystallized for purification. In other words, a pure adipic acid can be obtained by recycling the obtained crude adipic acid to a purification step in the production of adipic acid.

On the other hand, the liquor left in a process of separating a succinic acid, in which process a urea-succinic acid adduct is decomposed to succinic acid and urea by treatment with an ion exchange resin or an alicyclic ether and the succinic acid is recovered in the form of crystals from the solution, may be recycled as a solvent for the starting acid mixture obtained as a by-product in the production of adipic acid, after the solvent is removed in case the liquor contains an alicyclic ether and as it is when the liquor contains other solvents and does not contain an alicyclic ether.

Though the foregoing description is made referring to the treatment of an acid mixture obtained as a by-product in the production of adipic acid by oxidation of cyclohexanol and cyclohexanone with nitric acid, this invention may of course be applied to the treatment of acid mixtures from other sources, for example, an acid mixture obtained as a by-product in the oxidation of cyclohexane.

EXAMPLE 1

100 g. of an acid mixture [( composition: 60% by weight of glutaric acid; 25% by weight of succinic acid; and 15% by weight of adipic acid; each percentage being based on the mixture) obtained by the following process: subjecting cyclohexanol and cyclohexanone to two-stage oxidation in the presence of ammonium metavanadate and copper, using nitric acid as a solvent, at 60° to 80° C. in the first stage and at 100° to 110° C. in the second stage under a pressure of 2 to 10 atm. to produce adipic acid; separating the produced adipic acid after it is crystallized out; removing the remaining catalysts out of the mother liquor; and then distilling off the nitric acid] and 80 g. of urea were dissolved in 200 g. of water at 60° C. The resulting solution was then cooled to and allowed to stand at 20° C. for 60 minutes to precipitate a urea-glutaric acid adduct. The precipitated glutaric acid adduct was separated from the solution by filtration to obtain 95 g. of glutaric acid adduct (including 48 g. of glutaric acid). The obtained urea-glutaric acid adduct was dissolved in 320 g. of water at 35° C. and treated with DOWEX 50WX-4 (trade name of a strongly acidic ion exchange resin manufactured and sold by DOW CHEMICAL CO., LTD., U.S.A.) to remove the urea. The solution with the urea removed was cooled to and allowed to stand at 20° C. after removal of almost all of the water under reduced pressure of 2 to 30 mmHg. to obtain 47 g. of glutaric acid having a purity of 98%.

On the other hand, 45 g. of urea was further added to the mother liquor with the urea-glutaric acid adduct removed and dissolved in the liquor at 60° C. Then, the liquor was cooled to and allowed to stand at 15° C. for 5 hours to precipitate a urea-succinic acid adduct. By filtration of the liquor, 50.3 g. of urea-succinic acid adduct (including 21.6 g. of succinic acid) was obtained. The urea-succinic acid adduct was dissolved in 300 g. of water at 30° C. and the solution was treated with the same strongly acidic ion exchange resin as mentioned above. 200 g. of water was distilled off from the thus treated solution. On cooling to and allowing to stand at 10° C., succinic acid crystallized out of the solution and 19.2 g. of succinic acid having a purity of 99.0% was obtained by filtration.

The mother liquid with the urea-succinic acid adduct removed was treated with the same strongly acidic ion exchange resin as mentioned above to remove urea. The liquor was then subjected to distillation to remove 100 g. of water and cooled to and allow to stand at 15° C. to crystallize crude adipic acid. By filtration, 12.1 g. of crude adipic acid was obtained. The thus obtained crude adipic acid contained 2.1% by weight of glutaric acid and 1.3% by weight of succinic acid. This crude adipic acid may be recycled to a purification step in the production of adipic acid to obtain pure adipic acid.

The urea adsorbed on the strongly acidic ion exchange resin was readily desorbed by hot water of 60° C. and recovered in the form of an aqueous solution of urea.

EXAMPLE 2

100 g. of an acid mixture [(composition: 60% by weight of glutaric acid; 25% by weight of succinic acid; and 15% by weight of adipic acid; each percentage being based on the mixture) obtained by the following process: subjecting cyclohexanol and cyclohexanone to two-stage oxidation in the presence of ammonium metavanadate and copper, using nitric acid as a solvent, at 60° to 80° C. in the first stage and at 100° to 110° C. in the second stage under a pressure of 2 to 10 atm. to produce adipic acid; separating the produced adipic acid after it is crystallized out; removing the remaining catalysts out of the mother liquor; and then distilling off the nitric acid] and 75 g. of urea were dissolved in 200 g. of water at 60° C. and then cooled at 15° C. for 50 minutes to deposit a urea-glutaric acid adduct. By filtration, 95.8 g. of urea-glutaric acid adduct (including 48.6 g. of glutaric acid) was obtained. The obtained adduct and 300 g. of dioxane were heated at 90° C. for 80 minutes and then cooled to and allowed to stand at 20° C. to deposit urea. The deposited urea was removed by filtration and the dioxane in the filtrate was distilled off under reduced pressure to obtain 48.6 g. of glutaric acid having a purity of 98.0%.

From the mother liquor with the urea-glutaric acid adduct removed, 100 g. of water was distilled off. On cooling to and allowing to stand at 20° C. for 4 hours, 48 g. of urea-succinic acid adduct (including 19 g. of succinic acid) crystallized out of the liquor. Then, the urea-succinic acid adduct was dissolved in 400 g. of dioxane at 90° C. for 90 minutes and subsequently the resulting solution was cooled to and allowed to stand at 30° C. to deposit urea. The urea was removed by filtration and 330 g. of dioxane in the filtrate was distilled off under reduced pressure. On cooling to and allowing to stand at 15° C., succinic acid crystallized out of the filtrate and by subsequent filtration, 17.8 g. of succinic acid having a purity of 98.1% was obtained.

The mother liquor with the urea-succinic acid adduct removed was treated with AMBERLITE IR-121 (trade name of a strongly acidic ion exchange resin manufactured and sold by ROHM AND HAAS, U.S.A.) to remove urea. 100 g. of water was then distilled off from the liquor. On cooling to and allowing to stand at 15° C., crude adipic acid crystallized out of the liquor. By filtration, 12.0 g. of crude adipic acid was obtained. The obtained crude adipic acid contained 2.6% by weight of glutaric acid and 0.8% by weight of succinic acid. This crude adipic acid may be recycled to a purification step in the production of adipic acid to obtain pure adipic acid.

EXAMPLE 3

100 g. of an acid mixture [(composition: 56% by weight of glutaric acid; 27% by weight of succinic acid; and 17% by weight of adipic acid; each percentage being based on the mixture) obtained by the following process: subjecting cyclohexanol and cyclohexanone to two-stage oxidation in the presence of ammonium metavanadate and copper, using nitric acid as a solvent, at 60° to 80° C. in the first stage and at 100° to 110° C. in the second stage under a pressure of 2 to 10 atm. to produce adipic acid; separating the produced adipic acid after it is crystallized out; removing the remaining catalysts out of the mother liquor; and then distilling off the nitric acid] and 68 g. of urea were dissolved in 400 g. of methanol at 50° C. and then cooled to and allowed to stand at 20° C. for 60 minutes to deposit a urea-glutaric acid adduct. By filtration, 85 g. of urea-glutaric acid adduct (including 42.5 g. of glutaric acid) was obtained. The obtained urea-glutaric acid adduct was dissolved in 600 g. of methanol at 50° C. and treated with AMBERLYST A 29 (trade name of a strongly basic ion exchange resin manufactured and sold by ROHM AND HAAS, U.S.A.). The glutaric acid adsorbed on the resin was desorbed by treating the resin with a strong acid to obtain 42 g. of glutaric acid having a purity of 99.2%.

14 g. of urea was further added to the mother liquor with the urea-glutaric acid adduct removed and dissolved at 50° C., then subjected to cooling to and allowing to stand at 15° C. for 5 hours to deposit a urea-succinic acid adduct. 44 g. of urea-succinic acid adduct (including 20 g. of succinic acid) was obtained by filtration. The thus obtained urea-succinic acid adduct was dissolved in 500 g. of methanol at 30° C. and treated with AMBERLYST 15 (trade name of a strongly acidic ion exchange resin manufactured and sold by ROHM AND HAAS, U.S.A.) to remove urea. Then, 300 g. of methanol was distilled off and the solution was cooled to and allowed to stand at 20° C. to deposit succinic acid. By filtration 17.9 g. of succinic acid having a purity of 98.3% was obtained.

The mother liquor with the urea-succinic acid adduct removed was treated with AMBERLYST 15 to remove urea and cooled to and allowed to stand at 15° C. after 200 g. of methanol had been distilled off, to deposit crude adipic acid. By subjecting the solution to filtration, 11.0 g. of crude adipic acid was obtained. The obtained crude adipic acid contained 1.8% by weight of glutaric acid and 1.6% by weight of succinic acid. This crude adipic acid may be recycled to a purification step in the production of adipic acid to obtain pure adipic acid.

The urea adsorbed on the strongly acidic ion exchange resin was treated with hot methanol at 50° to 55° C. to be desorbed and recovered in the form of a methanol solution of urea.

EXAMPLE 4

100 g. of an acid mixture [(composition: 54% by weight of glutaric acid; 25% by weight of succinic acid; and 21% by weight of adipic acid; each percentage being based on the mixture) obtained by the following process: subjecting cyclohexanol and cyclohexanone to two-stage oxidation in the presence of ammonium metavanadate and copper, using nitric acid as a solvent, at 60° to 80° C. in the first stage and at 100° to 110° C. in the second stage under a pressure of 2 to 10 atm. to produce adipic acid; separating the produced adipic acid after it is crystallized out; removing the remaining catalysts out of the mother liquor; and then distilling off the nitric acid] and 80 g. of urea were dissolved in 250 g. of water at 60° C. and subsequently cooled to and allowed to stand at 15° C. for 50 minutes to deposit a urea-glutaric acid adduct. The urea-glutaric acid adduct was separated by filtration and 90 g. of urea-glutaric acid adduct (including 46 g. of glutaric acid) was obtained. The obtained urea-glutaric acid was dissolved in 370 g. of water at 35° C. and treated with DOWEX 50WX-4 as used in Example 1 to remove urea. Almost all of water was removed from the solution under reduced pressure and the solution was cooled to and allowed to stand at 20° C. to deposit glutaric acid. 45 g. of glutaric acid having a purity of 98.7% was obtained by filtration.

40 g. of urea was further added to the mother liquor with the urea-glutaric acid adduct removed and dissolved therein at 60° C. On cooling to and allowing to stand at 15° C. for 5 hours, a urea-succinic acid adduct crystallized out of the solution. By filtration, 50.7 g. of urea-succinic acid adduct (including 20.6 g. of succinic acid) was obtained.

The urea-succinic acid adduct was dissolved in 300 g. of water at 30° C. and treated with DOWEX 50WX-4 as mentioned above. 200 g. of water was then removed from the solution and the solution was cooled to and allowed to stand at 10° C. to deposit succinic acid. 18.7 g. of succinic acid having a purity of 98.8% was obtained by filtration.

The mother liquor with the urea-succinic acid adduct removed was treated with a column of the same strongly acidic ion exchange resin to remove urea. After 120 g. of water was further distilled off, the treated liquid was cooled to and allowed to stand at 15° C. to deposit crude adipic acid. 11.9 g. of crude adipic acid was obtained by filtration. The obtained crude adipic acid contained 2.1% by weight of glutaric acid and 1.3% by weight of succinic acid and may be recycled to a purification step in the production of adipic acid to obtain pure adipic acid.

EXAMPLE 5

100 g. of an acid mixture [(composition: 53% by weight of glutaric acid; 35% by weight of succinic acid; and 12% by weight of adipic acid; each percentage being based on the mixture) obtained by the following process: air oxidizing cyclohexanol and cyclohexanone in the presence of manganese acetate and copper, using acetic acid as a solvent, at 70° to 80° C. under a pressure of 5 atm. for 6 hours to produce adipic acid; separating the produced adipic acid in the form of crystals; removing the remaining catalysts out of the mother liquor; and distilling off the acetic acid] and 70 g. of urea were dissolved in 400 g. of ethanol at 50° C. and then cooled to and allowed to stand at 20° C. for 60 minutes to deposit a urea-glutaric acid adduct. By filtration 75 g. of urea-glutaric acid adduct (including 38 g. of glutaric acid) was obtained which was then subjected to heating at 80° C. for 70 minutes together with 450 g. of tetrahydrofuran. On cooling to and allowing to stand at 20° C., urea was deposited and removed by filtration. Subsequently, tetrahydrofuran in the filtrate was distilled off to obtain 38 g. of glutaric acid having a purity of 98.1%.

35 g. of urea was further added to the mother liquor with the urea-succinic acid adduct removed and dissolved therein at 50° C. The solution was then cooled to and allowed to stand at 15° C. for 5 hours to obtain 70 g. of urea-succinic acid adduct (including 32 g. of succinic acid). The obtained urea-succinic acid adduct was heated together with 500 g. of tetrahydrofuran at 90° C. for 70 minutes. On cooling to and allowing to stand at 20° C., urea crystallized out of the solution and was removed by filtration. The filtrate was then subjected to distillation until 360 g. of tetrahydrofuran was removed and cooled to and allowed to stand at 15° C. to obtain 28.8 g. of succinic acid having a purity of 98.3%.

The mother liquor with the urea-succinic acid adduct removed was treated with AMBERLYST 15 as used in Example 3 to remove urea. 200 g. of ethanol was distilled off from the filtrate with urea removed. On cooling to and allowing to stand at 15° C., crude adipic acid crystallized out of the filtrate and 9.3 g. of crude adipic acid was obtained by filtration. The obtained crude adipic acid contained 2.8% by weight of glutaric acid and 1.1% by weight of succinic acid and may be recycled to a purification step in the production of adipic acid to obtain pure adipic acid.

EXAMPLE 6

100 g. of an acid mixture [(composition: 69% by weight of glutaric acid; 27% by weight of succinic acid; and 4% by weight of adipic acid; each percentage being based on the mixture) obtained by dissolving the acid mixture as used in Example 1 in 200 g. of water at 60° C., allowing the resulting solution to cool to and stand at room temperature until adipic acid crystallized out of the solution, filtering the solution to remove the adipic acid and further removing water in the mother liquor] and 69 g. of urea were dissolved in 200 g. of water at 60° C. and the solution was then cooled to and allowed to stand at 15° C. for 80 minutes to crystallize a urea-glutaric acid adduct out of the solution. By filtration, 101 g. of urea-glutaric acid adduct (including 50 g. of glutaric acid) was obtained. The obtained urea-glutaric acid adduct was dissolved in 300 g. of water at 35° C. and the resulting solution was treated with DOWEX 50WX-4 as used in Example 1 to remove urea and subsequently cooled to and allowed to stand at 20° C., after almost all of water had been removed under reduced pressure, to obtain 49 g. of glutaric acid having a purity of 98%.

50 g. of urea was further added to the mother liquor with the urea-glutaric acid adduct removed and dissolved at 60° C. The resulting solution was then cooled to and allowed to stand at 15° C. for 5 hours to crystallize a urea-succinic acid adduct out of the solution. By filtration, 52 g. of urea-succinic acid adduct (including 22.0 g. of succinic acid) was obtained. Subsequently, the urea-succinic acid adduct was dissolved in 300 g. of water at 30° C. and the resulting solution was treated with the same strongly acidic ion exchange resin as mentioned above to remove urea. 200 g. of water was then distilled off from the treated solution and the solution was cooled to and allowed to stand at 10° C. to crystallize succinic acid. By filtration, 20 g. of succinic acid having a purity of 98% was obtained.

The mother liquor with the urea-succinic acid removed was treated with the same strongly acidic ion exchange resin as mentioned above to remove urea. The thus treated liquor was cooled to and allowed to stand at 16° C., after 100 g. of water had been removed, to obtain 12.2 g. of crude adipic acid. The obtained crude adipic acid contained 2.5% by weight of glutaric acid and 1.0% by weight of succinic acid and may be recycled to a purification step in the producttion of adipic acid to obtain pure adipic acid. The urea adsorbed on the strongly acidic ion exchange resin may be recovered in the form of aqueous solution of urea by treating the resin with hot water of 60° C.

EXAMPLE 7

100 g. of an acid mixture [(composition: 53% by weight of glutaric acid; 28% by weight of succinic acid; and 19% by weight of adipic acid; each percentage being based on the mixture) obtained by oxidizing cyclohexane with an oxygen containing gas and removing cyclohexanol, cyclohexanone, cyclohexane, monobasic acid, hydroxy acid and part of adipic acid out of the resulting oxidation product] and 72 g. of urea were dissolved in 400 g. of methanol at 50° C. On subsequent cooling to and allowing to stand at 20° C. for 50 minutes, a urea-glutaric acid adduct crystallized out of the solution. By filtration, 89 g. of urea-glutaric acid adduct (including 44 g. of glutaric acid) was obtained. The obtained urea-glutaric acid adduct was dissolved in 600 g. of methanol at 50° C. The resulting solution was treated with AMBERLYST A 29 as used in Example 3. The glutaric acid adsorbed on the resin was desorbed by treating the resin with a strong acid and 43 g. of glutaric acid having a purity of 98.5% was obtained.

35 g. of urea was further added to the mother liquor with the urea-glutaric acid adduct removed and dissolved at 50° C. The resulting solution was then cooled to and allowed to stand at 15° C. for 5 hours to crystallize a urea-succinic acid adduct out of the solution. By filtration, 47 g. of urea-succinic acid adduct (including 21 g. of succinic acid) was obtained. The obtained urea-succinic acid adduct was dissolved in 500 g. of methanol at 30° C. and the resulting solution was treated with AMBERLYST 15 as used in Example 3 to remove urea. After removal of 300 g. of methanol, the solution was cooled to and allowed to stand at 20° C. to precipitate succinic acid. By filtration, 18 g. of succinic acid having a purity of 97.9% was obtained.

The mother liquor with the urea-succinic acid adduct removed was treated with the same strongly acidic ion exchange resin as mentioned above to remove urea. Subsequently, 200 g. of methanol was removed and the solution was cooled to and allowed to stand at 15° C. to deposit crude adipic acid. By filtration, 21 g. of crude adipic acid was obtained. The obtained crude adipic acid contained 2.1% by weight of glutaric acid and 1.8% by weight of succinic acid and may be recycled to a purification step in the production of adipic acid to obtain pure adipic acid. The urea adsorbed on the strongly acidic ion exchange resin was desorbed by treating the resin with hot methanol of 50° to 55° C. to be recovered in the form of a methanol solution of urea.

EXAMPLE 8

50 g. of urea-succinic acid adduct obtained in the same manner as Example 1 was dissolved in 300 g. of water at 30° C. and the resulting solution was treated with the same strongly acidic ion exchange resin as used in Example 1 to remove urea. Then, 200 g. of water was distilled off from the treated solution and cooled to and allowed to stand at 20° C. for 3 hours to precipitate succinic acid. By filtration, 18 g. of succinic acid having a purity of 99% was obtained.

95 g. of the mother liquor with the urea-succinic acid adduct removed (containing 6 g. of glutaric acid and 3 g. of succinic acid) was recycled to 100 g. of acid mixture identical with that in Example 1 and dissolved in 180 g. of water together with 90 g. of urea at 60° C. The solution was then cooled to and allowed to stand at 20° C. for 60 minutes to precipitate a urea-glutaric acid adduct. By filtration, 101 g. of urea-glutaric acid adduct (including 54 g. of glutaric acid) was obtained. The obtained urea-glutaric acid adduct was dissolved in 350 g. of water at 35° C. and the solution was treated with the same strongly acidic ion exchange resin as used in Example 1 to remove urea. After almost all of water was removed from the solution under reduced pressure, the solution was cooled to and allowed to stand at 20° C. to obtain 53 g. of glutaric acid having a purity of 98%

50 g. of urea was further added to the mother liquor with the glutaric acid adduct removed and dissolved at 60° C. The resulting solution was cooled to and allowed to stand at 15° C. for 4 hours to precipitate a urea-succinic acid adduct. By filtration, 51 g. of urea-succinic acid adduct (including 23 g. of succinic acid) was obtained. The obtained urea-succinic acid adduct was then dissolved in 300 g. of water at 30° C. and the solution was treated with the same strongly acidic ion exchange resin as mentioned above to remove urea. 200 g. of water was removed from the treated solution and on subsequent cooling to and allowing to stand at 10° C. for 3 hours, succinic acid crystallized out of the solution. By filtration, 20 g. of succinic acid having a purity of 99% was obtained.

The mother liquor with the urea-succinic acid adduct removed was treated with the same strongly acidic ion exchange resin as mentioned above to remove urea. After removal of 90 g. of water, the treated mother liquor was cooled to and allowed to stand at 20° C. to deposit crude adipic acid. By filtration, 11.0 g. of crude adipic acid was obtained. The obtained crude adipic acid contained 1.8% by weight of glutaric acid and 1.4% by weight of succinic acid and may be recycled to a purification step in the production of adipic acid to obtain pure adipic acid. The urea adsorbed on the strongly acidic ion exchange resin was recovered in the form of an aqueous solution of urea by treating the resin with hot water of 60° C.

What is claimed is:

1. A method for obtaining glutaric acid, succinic acid, and adipic acid from an acid mixture obtained as a by-product in the production of adipic acid and comprising 50 to 75% by weight based on the mixture of glutaric acid, 15 to 35% by weight based on the mixture of succinic acid and 7 to 30% by weight based on the mixture of adipic acid, which comprises the steps of:

(1) contacting the acid mixture with urea in solution to deposit a urea-glutaric acid adduct so that the weight ratio of glutaric acid remaining in the solution to succinic acid is 1.4 or less;
  the urea being employed in an amount of 1 to 2 moles per mole of the acid mixture;
  separating the deposited urea-glutaric acid adduct out of the solution;

(2) adding an additional portion of urea to the solution and/or concentrating the solution obtained in the step (1) to deposit a urea-succinic acid adduct; separating the deposited urea-succinic acid adduct out of the solution; and (3) decomposing the separated urea-dicarboxylic acid adducts each into respective dicarboxylic acids and urea.

2. A method as set forth in claim 1, wherein in the step (1) the urea is employed in an amount of 1.8 moles or less but more than 1.5 moles.

3. A method as set forth in claim 1, wherein in the step(2) the urea is employed in an amount of 0.2 to 2.0 moles per mole of the starting acid mixture.

4. A method as set forth in claim 1, wherein the contacting is effected in a solution of water, an alcohol, a ketone and/or an ester.

5. A method as set forth in claim 1, wherein in the step (1) the concentration of the acid mixture in the solution is 5% or more by weight based on the solution.

6. A method as set forth in claim 1, wherein the separated urea-dicarboxylic acid adducts are each decomposed by an ion exchange resin into respective dicarboxylic acids and urea.

7. A method as set forth in claim 6, wherein the ion exchange resin is a strongly acidic ion exchange resin.

8. A method as set forth in claim 7, wherein the urea adsorbed on the strongly acidic ion exchange resin is desorbed by hot water and recycled to the urea to be employed in the step (1) and/or step (2).

9. A method as set forth in claim 7, wherein the urea adsorbed on the strongly acidic ion exchange resin is desorbed by hot organic solvent and recycled to the urea to be employed in the step (1) and/or step (2).

10. A method as set forth in claim 1, wherein the separated urea-dicarboxylic acid adducts are each treated with an alicyclic ether to decompose the adducts into respective dicarboxylic acids and urea.

11. A method as set forth in claim 1, which further comprises purifying the succinic acid obtained in the step (3) by crystallization from the solution and recycling the resulting solution containing glutaric acid to the acid mixture in the step (1).

12. A method as set forth in claim 1, wherein the solution obtained in the step (2) is treated with a strongly acidic ion exchange resin and then concentrated to deposit adipic acid.

13. A method as set forth in claim 1, wherein the solution obtained in the step (2) is concentrated to deposit adipic acid and a urea-adipic acid adduct, which are then treated with an ion exchange resin to isolate the adipic acid.

14. A method as set forth in claim 13, wherein the ion exchange resin is a strongly acidic ion exchange resin.

15. A method as set forth in claim 14, wherein the urea adsorbed on the strongly acidic ion exchange resin is treated with hot water to desorb the urea and recycled to the urea to be employed in the step (1) and/or step (2).

16. A method as set forth in claim 14, wherein the urea adsorbed on the strongly acidic ion exchange resin is treated with a hot organic solvent to desorb the urea and recycled to the urea to be employed in the step (1) and/or step (2).

17. A method as set forth in claim 1, wherein the solution obtained in the step (2) is concentrated to deposit adipic acid and a urea-adipic acid adduct, which are then treated with an alicyclic ether to separate adipic acid.

18. A method for obtaining glutaric acid, succinic acid, and adipic acid from an acid mixture obtained as a by-product in the production of adipic acid and comprising 50 to 75% by weight based on the mixture of glutaric acid, 15 to 35% by weight based on the mixture of succinic acid and 7 to 30% by weight based on the mixture of adipic acid, which comprises the steps of:

(1) contacting the acid mixture with urea in solution to deposit a urea-glutaric acid adduct so that the weight ratio of glutaric acid remaining in the solution to succinic acid is 1.4 or less.
  the urea being employed in an amount of 1 to 2 moles per mole of the acid mixture;
  separating the deposited urea-glutaric acid adduct out of the solution;

(2) adding an additional portion of urea to the solution and/or concentrating the solution obtained in the step (1) to deposit a urea-succinic acid adduct;
  separating the deposited urea-succinic acid adduct out of the solution;
  treating the solution obtained in the step (2) with a strong acidic ion exchange resin to remove urea, concentrating the treated solution to obtain a crude adipic acid deposit and
  recycling the crude adipic acid to a recystallization step to produce pure adipic acid.

* * * * *